United States Patent [19]

Frank et al.

[11] 4,092,980

[45] June 6, 1978

[54] FIBRINOGEN MONITOR

[75] Inventors: Donald H. Frank, Deerfield; J. Fred Jeffries, Waukegan; Mary C. Swanson, Lincolnwood, all of Ill.; Thomas L. Erb; James D. Hall, both of Austin, Tex.

[73] Assignee: G. D. Searle & Co., Chicago, Ill.

[21] Appl. No.: 648,254

[22] Filed: Jan. 12, 1976

[51] Int. Cl.² .............................................. A61B 6/00
[52] U.S. Cl. .................................. 128/2 A; 250/363 S
[58] Field of Search .......................... 128/2 A, 2.05 R; 250/363 S; 313/364 S

[56] References Cited

U.S. PATENT DOCUMENTS

| 3,509,341 | 4/1970 | Hindel et al. | 250/363 S |
| 3,827,427 | 8/1974 | Knoll | 128/2 A |
| 3,890,355 | 6/1975 | Brunnett et al. | 250/363 S |
| 3,899,675 | 8/1975 | Floyd | 250/363 S |

FOREIGN PATENT DOCUMENTS 1,466,902   5/1969   Germany .............................. 128/2 A

*Primary Examiner*—Kyle L. Howell
*Attorney, Agent, or Firm*—Dennis O. Kraft; Peter J. Sgarbossa

[57] ABSTRACT

A fibrinogen monitor for use in monitoring the concentration of iodinated fibrinogen distribution in the calf and thigh veins of bed-restricted patients. The fibrinogen monitor is an improved scintillation detector which a hospital staff member can manipulate using one hand to detect and record scintillation events at measured points along the leg of a patient while leaving the other hand free to aid in positioning the leg. The output of the monitor is digitized and provided both as a visual display and as a hard-copy record. The geometrical configuration of the probe of the monitor provides for increased sensitivity to gamma radiation without an attendant increase in probe size.

27 Claims, 5 Drawing Figures

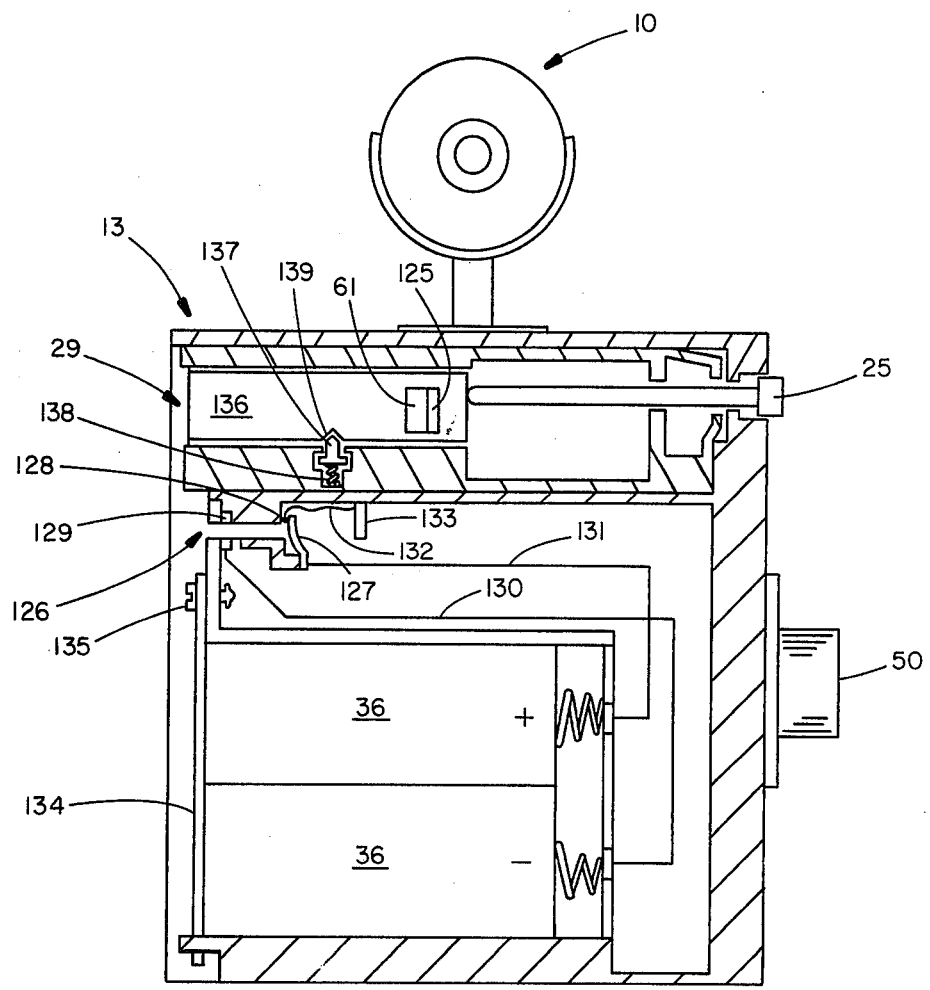
FIG. 2
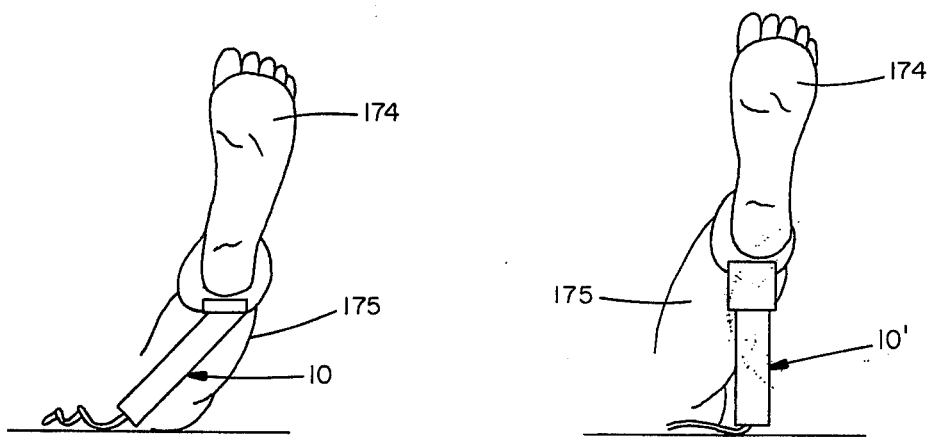
FIG. 4A
FIG. 4B
PRIOR ART

FIBRINOGEN MONITOR

BACKGROUND OF THE INVENTION

The monitoring of radiolabeled fibrinogen is a hospital technique which is used in an attempt to detect the early formation of thrombii (clots) in patients so that medical treatment may be initiated. For thrombosis to occur, two conditions are necessary, shock and hemostasis (static blood). In a hospital environment, shock to the system of a patient may be the result of different causes, but most typically results from surgery or myocardial infarction (heart attack). The hemostasis is most prevalent in the lower extremities of patients who are bed ridden and inactive. A thrombus in a patient typically develops in the deep veins of the legs and may break away and be flushed by the blood stream into the lungs resulting in pulmonary embolism. Pulmonary embolism is an extremely serious complication to any patient. A significant percentage of pulmonary embolii in patients result in fatalities.

Fibrinogen is normally present in the system of a patient and it plays a key role in the formation of a thrombus as it is incorporated into the thrombus. Thrombus formation may occur immediately after surgery or may be delayed for many days. Fibrinogen labelled with Iodine-125 is the most convenient way of detecting and following the progress of deep vein thrombosis.

Fibrinogen monitoring has been proven accurate in the detection of deep vein thrombosis between mid-thigh and the calf of a patient's leg. Although the clinical correlation between deep vein thrombosis and pulmonary embolii from the deep veins is still under investigation, there is a strong inference of high risk which may be drawn from the detection of deep vein clot formation. Once detected, preventive treatment may be prescribed, typically the administration of an anticoagulant drug such as heparin.

There is typically a higher risk of thrombosis to patients who are over 40 years of age, who are overweight, and who smoke. While the danger of thrombosis is most acute to hospital patients who have undergone surgery, it is thought that thrombosis may be a problem in stroke patients, out patients, obstetric-gynecology patients and any patient suffering from hypercoagubility of the blood from one of a number of causes. In fact, the development of thrombosis and resulting pulmonary embolism is considered by some to be the leading cause of unexpected hospital death.

Radiolabeled fibrinogen is considered to be the best pharmaceutical available for use in detecting post surgical deep vein thrombosis since labeled material can be injected pre-operatively. Routine patient monitoring conducted over a 4 or 5 day period post-operatively is thereafter performed. A second injection may be required if further monitoring is indicated. While various labeling substances have been used with fibrinogen, the radioisotopes of iodine are considered to be the best labels or tags. While each of these radioisotopes has its own advantages and disadvantages, Iodine-125 is the most broadly used and seems to be the most satisfactory radioisotope for use in labeling fibrinogen to allow deep vein thrombosis monitoring of patients in prognostic studies. (For diagnostic studies or formed clots other isotopes may be superior). Iodine-125 emits gamma radiation with characteristic energy peaks. A differential discriminator may be used to bracket these peaks and isolate an energy range from about 20 to 100 thousand electron volts both from higher energy and lower energy background.

In a typical fibrinogen monitoring situation, a patient is injected with 100 microcuries of Iodine-125 in one milligram of fibrinogen pre-operatively. While the patient is recovering from surgery, fibrinogen monitoring is conducted. In this procedure, a portable sodium iodide scintillation detector is placed over the heart for a reference reading to normalize to the concentration of I-125 in the blood. The detector is then moved longitudinally down the anterior of the thigh and posterior of the calf of each leg in approximately two inch increments. Readings are recorded on a patient record chart at each increment as percentages of the count obtained over the heart (Precordial Count). The patient is checked and rechecked in this manner at approximately 24 hour intervals, or more frequently if indicated. If the counts at any measuring point along the patient's leg exceeds the reference rate over the heart by more than 20%, or if the counts at any one segment exceed the two adjacent segments or the corresponding point on the other leg by more than 20%, a thrombus is considered to be present.

There are several serious deficiencies in all the instruments presently available for use in fibrinogen monitoring, however. The monitoring process is extremely time consuming because the hospital staff member manipulating the fibrinogen monitor must use one hand to position the patient's leg and hold the scintillation detector probe in position while operating a separate processing and display console and manually recording the readings obtained on a patient record chart with the other hand, or alternatively a second staff member is required to record the readings that the monitoring staff member is acquiring as the acquisition process often requires the use of both hands. In addition, there are many instances where only a small number of radioactive events are detected from the labeled fibrinogen. In this connection, the present instruments provide no safeguard against the measurement and recordation of statistically insignificant data due to an extremely low level of fibrinogen concentration or because of mispositioning of the probe containing the photomultiplier tube and scintillation crystal. Statistical fluctuations are of particular concern where the instrument operator is deriving readings from an analogue meter, as is the case with the instruments presently available.

A further inadequacy of the present instrumentation is the form of display, which produces a representation of the pulse count rate from the scintillation probe only as the position of a needle on a ratemeter scale. The length of time required to ascertain that the needle has stabilized and to visually interpolate a reading from the ratemeter scale unnecessarily lengthens the time required to obtain each reading at each measurement point along the patient's legs.

SUMMARY OF THE INVENTION

The fibrinogen monitor of the present invention is designed to obviate the foregoing deficiencies in the scintillation detectors presently available. The principal objects of the invention are to reduce the amount of time required by the hospital staff member operating the instrument to take the various readings at the measurement points on the patient's legs and to considerably reduce the chance for erroneous readings. Accordingly, a scintillation detector probe is provided in which the scintillation detector is mounted at an angle with respect to the photosensitive face of the photomultiplier tube.

This geometrical configuration allows the probe to be used in areas of smaller clearance on the anterior and the posterior sides of the patient's legs so that the patient's legs do not have to be separated as far and/or elevated as high as is necessary with the geometrical configuration of conventional scintillation probes. Another object of the invention is to provide the instrument operator with a fibrinogen monitor in which the measurement and recording functions and probe positioning can be performed with a single hand, leaving the other hand of the operator free to aid in positioning and immobilizing the patient's leg. This feature substantially increases the uniformity of measurements using the fibrinogen monitor and thereby improves the reliability of the results obtained.

Another object of the invention is to provide a scintillation detector which automatically provides a digital display of data, thus obviating the need for operator interpolation from a ratemeter scale. Preferably, all of the temporary visual displays relating to the recordation of data employ light emitting diodes.

A further object of the invention is to provide a fibrinogen monitor which upon operator command, automatically prints the data obtained from the sequential measurements in a format which is readily matched to a data logging form. The instrument data is printed on a coiled paper tape as it is unrolled and expelled from the data processing portion of the fibrinogen monitor.

The length of tape containing the data for a particular patient is printed with spacing corresponding to the proper spacing on a data logging form. The tape can thereby be attached directly to the form so that the data readings are coordinated with the measurement point designations on the form.

A further object of the invention is to provide a fibrinogen monitor which includes an error indicator when the data rate falls below a level which is acceptable for the particular counting interval being used. This might be due either to decay of the radioisotope dose or improper probe positioning, as was discussed previously, and due to too short a counting interval. In either event, the recordation of statistically questionable data is prevented.

Another object of the invention is to provide for an adjustment of the counting time within the measurement sequence without the need for manually recomputing the data to a format compatible with data previously obtained. In this way, a greater number of counts can be obtained at points where low level of radioactivity exists in order to maintain adequate statistical accuracy. Coordination of the varying counting time is performed automatically so that all of the data at the various measurement points is displayed and recorded as a percentage of the reference count rate of pulses when the probe is positioned directly over the patient's heart.

Another object of the invention is the provision of an internal radioactive source for reproducible calibration of the instrument. When the probe is in the storage position, it is located near this source so that calibration is easily performed in a reproducible manner.

Another object of the invention is the provision of means to prevent the fibrinogen monitor operator from failing to measure and record the reference (Precordial) count rate with the probe positioned directly over the patient's heart prior to measuring radioactivity at spaced points along the patient's legs.

DESCRIPTION OF THE INVENTION

The various features and advantages of the fibrinogen monitor of this invention will appear more fully with reference to the accompanying drawings in which:

FIG. 2 is a side elevational cross sectional view of the pulse processing and display unit.

FIG. 4A is a diagram facing the soles of the feet of a patient illustrating the use of the probe of the present invention.

FIG. 4B is a diagram facing the soles of the feet of a patient illustrating the use of a prior art probe.

Figure 3:
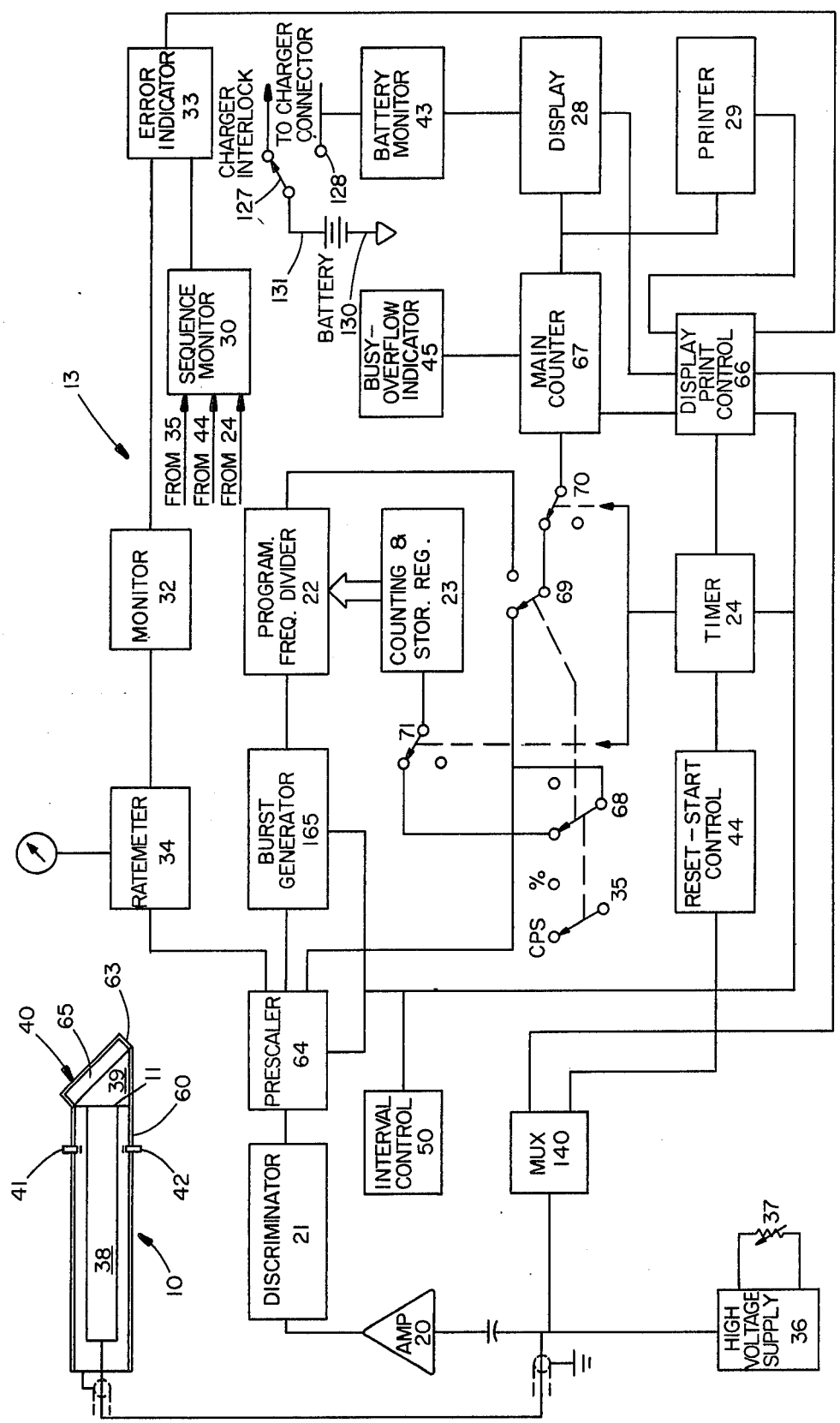
FIG. 3 is a diagram of the probe and electrical connections and components of the fibrinogen monitor.

Referring now to FIG. 3, there is shown an instrument for detecting the formation of blood clots (thrombii) in a patient who has been injected with a tracer quantity of radioactive fibrinogen. This instrument includes a scintillation probe 10 having a photomultiplier tube 38 with a flat photosensitive surface 11. The photomultiplier tube 38 is approximately 6 inches long with a 1⅛ inch diameter barrel. The photosensitive surface 11 is approximately 0.9 inches in diameter. A laminar scintillator 40 including a scintillation crystal 65 is aligned at an angle with respect to the photosensitive surface 11. This angle is preferably 45°. The scintillator member 40 includes an aluminum foil 63 serving as a moisture barrier and surrounding its exposed surfaces other than the surface in contact with the light guide 39 which is interposed between and optically couples the scintillator member 40 and the photosensitive surface 11. From this configuration it can be seen that the area of the scintillator member 40 is greater than the area of the photosensitive surface 11. This allows a greater number of radioactive events to be detected than would be possible were the scintillator member a flat disc positioned in direct contact with photosensitive surface 11 as in conventional scintillation detectors.

An example of the advantageous use of the probe 10 is illustrated in FIG. 4A. In this drawing it can be seen that a patient's leg 175 and foot 174 must be elevated a slight distance for the probe 10 to be placed in position along the patient'calf. From FIG. 4B, it can be seen that substantially greater elevation is necessary with a conventional probe 10' of the same length.

The scintillation crystal 65 in the scintillator member 40 is formed of thallium activated sodium iodide. The probe casing 60 is constructed of chrome plated brass. An electrical signal control element includes a start count button 42 and a print button 41 protruding through the casing 60. These buttons are finger operable actuating means and when pressed, activate appropriate circuits in the pulse processing and display unit 13 remotely located from the scintillation probe 10. The pulse processing and display unit 13 includes a differential discriminator 21 for receiving electrical pulses from the photodetector 38 and a frequency-phase-amplitude demultiplexing circuit 140 for recognizing start, print and scintillation event signals coming into the unit 13 on a common wire from the probe 10. Pulse recorder means is connected to the output of the differential discriminator 21. Operation of the pulse recorder means is controlled by the electrical signal control element which includes the print button 41 and the start count button 42. The pulse recorder means includes an interval control unit with interval control switch 50, reset-start control 44, a timer 24, a mode selection switch 35, and digital count rate and percentage mode circuitry and analog ratemeter circuitry. The digital count rate mode circuitry includes a prescaler 64 and a main counter 67. The percentage mode circuitry includes the foregoing count rate mode circuitry elements and also a burst generator circuit 165, a base count digital counting and storage register 23, and a programmable frequency divider 22.

Figure 1:
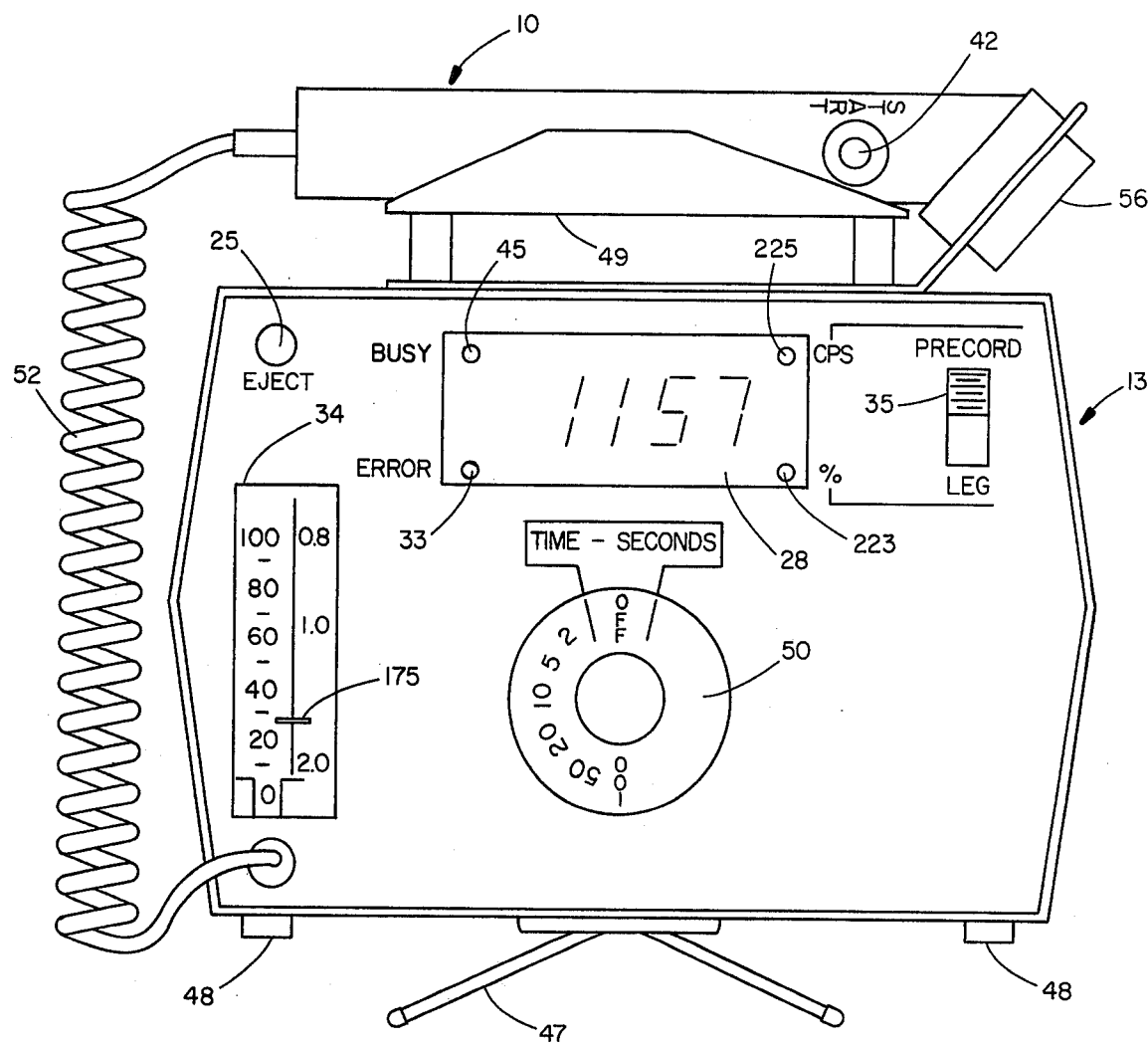
FIG. 1 illustrates the control panel of a pulse processing and display unit of the fibrinogen monitor.

The input pulses from the discriminator 21, which is a single channel pulse height (energy) analyzer, come into the prescaler 24, which contains a pair of decade scalers and a one-of-eight selector, which selects one of the scaler outputs to feed to an analog ratemeter 34. This selection is based on the setting of the counting interval control 50. When the instrument is operated in the count rate mode, the pickoff from the decade scalers in prescaler 64 is selected by a one-of-four selector in the prescaler 64. This one-of-four selector is controlled by two bits of the time code which is stored in the interval control 50. In the count rate mode, the output line from prescaler 64 is fed through switches 68 and 71 to the counting and storage register 23. Switches 68 and 69 are connected to operate in a slave relationship with switch 35. The switches 70 and 71 are controlled by timer 24 and are thrown to the positions opposite the positions indicated in FIG. 3 after the counting interval has elapsed. At this point, the digital count of pulses is stored in the counting and storage register 23 and in the main counter 67. It can be seen that counting and storage register 23 is operably connected to the differential energy discriminator 21, and to the timer 24, and accumulates pulses from the differential discriminator 21 for an interval of time determined under the control of the timer 24. This interval of time begins upon actuation of the button 42 in the control element 10 and terminates at the end of the counting interval set by the interval control 50 by the opening of switches 70 and 71. Accordingly, the count rate mode circuitry is operative when the mode select switch 35 is in the CPS (Counts Per Second) position as indicated in FIG. 3 and also labeled PRECORD (for precordial) in FIG. 1. During the counting interval a BUSY-OVERFLOW light emitting diode (LED) 45 is illuminated on the face panel of the instrument, as depicted in FIG. 1. At the end of the counting period, the number of counts appears on an LED digital display 28, unless there is an overflow count in which case the BUSY-OVERFLOW LED 45 will flash on and off until a new count is initiated or unless the count rate drops below an acceptable level in which case the ERROR LED 33 will be illuminated until a new count is initiated. When the mode select switch 35 is changed to the percent or LEG position, incoming pulses are routed through the percentage mode circuitry. The output of prescaler 64, which now divides the pulses received by 10, is connected to the burst generator 165.

The burst generator 165 operates by opening a gate to its high frequency oscillator and counting out a fixed number of pulses each time that it is triggered by an input pulse from the prescaler. The net effect is that the burst counter produces a stop burst signal after 10, 20, 50, 100, 200, 500, 1000, 2000, or 5000 pulses, depending on the time interval setting during each percent mode count and on the time interval setting during the latest count rate mode count.

The output of the burst generator 165 is fed into the programmable divider 22 which serves to divide the output of the burst generator by the count from the last count rate mode operation which is stored in counting and storage register 23.

The programmable divider 22 is a four decade presettable down counter which operates by loading in the data from counting and storage register 23, counting down to zero as pulses are received from burst generator 165, reloading the data from digital storage unit 23, counting down to zero again etc. One output is generated after each count down. Thus if the count rate mode count stored in the counting and storage register 23 is N, then the programmable divider 22 will put out one pulse for every N input pulses.

The output pulses from the programmable divider 22 are fed through the switch 69 into the main counter 67. In the percent mode, the switch 70 is in the position opposite that in FIG. 3 and the main counter 67 receives inputs from the programmable divider 22 to display the ratio of counts to the base count as a percentage on display unit 28.

This base count is always performed with the mode select switch 35 in the count rate position. Thereafter, for the sequential measurement at points along the patient's legs, the measurements are performed with the mode select switch 35 in the percent position. The percent figure displayed in the LED display 28 is the newly acquired number of pulse counts from the discriminator 21 expressed as a percentage of the reference count in the counting and storage register 23.

Upon observing this display, the instrument operator may press the button 41 on the probe 10, and the data displayed on display unit 28 will be printed by the printer 29.

For detecting an error condition which could be caused by an abnormally low pulse count rate at any of the measurement points along the patient's legs, there is provided circuitry which culminates in the error indicator 33. This circuitry includes analog pulse rate circuit 34 which continuously puts out a voltage proportional to the pulses per second from the discriminator 21 times the time interval set into interval control circuit 50. This rate proportional voltage is displayed on the panel meter of the ratemeter 34 as illustrated in FIG. 1. In addition, a monitor circuit 32 is connected to the output of ratemeter 34 to produce a rejection signal output whenever the rate of pulses from the discriminator times the time interval setting is such that the counting time interval (seconds) set into the time interval control 50 times the pulse rate from the discriminator 21 (pulses per second) is such that the final digital count in either the count rate or percentage mode will be based on an accumulation of pulses in discriminator 21 which are not statistically significant. When the count rate times the time interval setting is less than the acceptable minimum, the resulting error signal illuminates the ERROR indicator 33, and disables the pulse recorder means and inhibits the Display/Print control 66 from allowing either the display or printing of the contents of main counter 67. A similar sequence error generated by the sequence monitor 30 is also connected to Display/Print control 66 to inhibit the operation of the pulse processing and display unit, including display and printing functions, when the mode selection switch 35 is in the Percent mode without first storing statistically significant data in the reference count storage register 23 while in the Precordial or Count Rate mode. This is due to the signal from the reset-start control 44. When the proper sequence is followed and a statistically significant pulse count is stored in the reference count storage register 23, no such actuating signal is passed to the sequence monitor circuit 30. However, if a statistically significant count has not been stored in the digital storage circuit 23, a signal is passed to the circuit 30 upon attempted start in the percent mode and the sequence monitor 30 illuminates the error indicator 33 sounds the audible alarm in the reject indicator 33, and inhibits the accumulation of pulses upon the starting of the timer 24. A switch is provided for the audible alarm to inhibit its operation whenever the monitor operator feels if might create excessive disturbance.

All of the various dials, adjustments, and indicators are illustrated in FIGS. 1 and 3. As previously explained, the digital display 28 is an LED digital display of the pulse count contained in the main counter 67. Illumination of the Busy-Overflow indicator 45 indicates that a count is in progress. Flashing of the Busy-Overflow indicator 45 indicates an overflow condition. Illumination of the Error Indicator 33 indicates that the pulse rate times the time interval was too low during or at the start of a counting operation or that a percent count was attempted without first completing a count rate count.

Illumination of the CPS (PRECORD) indicator 255 or the % (LEG) indicator 233 indicates the mode in which the presently displayed data was taken.

The counting time interval control 50 may be adjusted in discrete increments to vary the counting time of measurement. The analog ratemeter 34 is used to provide a visual signal of the relative pulse rate from discriminator 21 and of the expected standard deviation of the data displayed on the LED display 28. The analog ratemeter scale sensitivity is controlled by the interval time switch 50. The ratemeter scale sensitivity is directly proportional to the interval set by the time switch 50. Thus the analog ratemeter reading will be directly proportional to actual pulse rate (pulses per second) from the discriminator 21 times the time interval setting of the interval control or time switch 50. Since the total pulse count accumulated during a count rate mode or a percent mode count will be the pulse rate times the time interval, the analog ratemeter reading will be a direct indication of the expected total accumulation of discriminator output pulses during the counting interval. This indication will hold true independent of time switch 50 setting.

As a direct indication of expected count accumulation the reading from the analog ratemeter 34 is also a direct indication of the expected standard deviation independent of the time switch setting. The analog ratemeter scale is thus marked in terms of expected standard deviation. This feature allows the operator to preview the expected statistical accuracy before making the count. If the indicated standard deviation is not good enough, the operator may change the setting of the time switch 50 to achieve an expected standard deviation consistent with the measurement objectives.

The isotope peaking control 37 actually adjusts the high voltage power supply 36 supplying the photomultiplier tube 38. This allows the fibrinogen monitor to be used with different radioisotopes although the radioisotope iodine 125 is most frequently used as the labeling substance.

The probe 10 is connected to the pulse processing and display unit 13 by means of a coiled cable 52. An amplifier 20 is provided to increase the signal strength between the probe 10 and the discriminator 21 in the pulse processing and display unit 13. A collapsible leg unit 47 allows the pulse processing and display unit 13 to be read in either a tilted position, as shown in FIG. 1, or resting flat on the rubber grommets 48.

The printer 29 is actuated by the button 41 in the electrical signal control element, and when actuated, prints the contents of the main control 67. As illustrated in FIG. 2, the printer 29 includes a cassette 136, which contains a single, coiled tape that is advanced past roller 61 through slot 125 in cassette 136 in the direction perpendicular to the plane of FIG. 2. The printer 29 is adjusted to leave predetermined spaced intervals between the printed material derived from successive outputs of the main counter 67.

The pulse process and display unit includes a rechargeable battery pack, containing 4 batteries 36, which may be secured in place in the unit 13 through a door 134. A fastening latch 135 secures the door 134 in place so that the contacts of the batteries are connected to the electrical leads 130 and 131. When the batteries are to be recharged, a conventional electrical jack (not shown) is inserted into the jack receptacle 126. Advancement of the jack breaks the electrical power circuit by forcing contact 127 away from contact 128 which is connected to an electrical terminal 133 by means of a wire 132. The batteries may thereby be recharged through leads 130 and 131 and the unit is rendered inoperative during charging. A battery monitor 43 causes the display on the display unit 28 to flash on and off when the voltage of the batteries has dropped to the point where recharging is required.

In inserting the cassette 136, the cassette is pushed into the unit 13 until the detent 137 engages the conical depression 139 in the underside of the cassette 136. The spring 138 is compressed to hold the cassette in place. To release the cassette, some slight force is required on eject button 25 to overcome the force of spring 138 when detent 137 disengages, cassette 136 springs to the rear of the unit 13 where it may be seized and removed.

A recess is defined in the carrying handle 49 of the pulse processing and display unit so that the scintillation probe 10 is snugly and removably seated in the cavity in a reproducible position with the face of the scintillator assembly against the check source 56. The stable low level radiation source 56 is provided for use in pulse amplitude calibration using the peaking adjustment 37 and to check the operation of the unit.

The foregoing detailed description of the invention disclosed is for purposes of illustration only, and should not be considered limiting, as various alternative configurations of the invention fall within the scope of the claims appended hereto.

We claim:

1. A portable instrument for use in detecting the formation of blood clots in a patient in whom a quantity of fibrinogen tracer-labelled with a radioisotope has been administered, said portable instrument comprising:

an axially elongated hand-held radiation monitoring probe having a radiation detecting member at one end thereof disposed at an angle to the longitudinal probe axis to thereby enable use of said probe in areas of small clearance on the patient's body such as the anterior and posterior sides of the patient's legs;

switch means disposed on said probe and manually actuatable by the user thereof with the same hand holding said probe to selectively generate a start count signal and a record count signal;

pulse processing means located remotely from said monitoring probe for counting, processing and recording the electrical pulses from said radiation detecting member upon receipt of said start count signal;

record means connected to the output of said pulse processing means for recording the processed pulse count upon receipt of said record count signal; and means to automatically disable said record means upon the receipt of a statistically insignificant number of pulses from said radiation detecting member, whereby a safeguard is provided against the measurement and recordation of statistically insignificant data due to an extremely low level of fibrinogen concentration or because of mispositioning of the radiation monitoring tube.

2. A portable instrument as claimed in claim 1, wherein said record means comprises a printer which includes a printing tape and adjustable means to advance said tape as printing occurs to leave predetermined spatial intervals between printed material derived from successively different outputs from said processing means.

3. An instrument for detecting the formation of blood clots in a patient who has been injected with a tracer quantity of radioactive fibrinogen comprising a scintillation probe including a photodetector having a flat photosensitive surface, a laminar scintillator member aligned at an angle with respect to said photosensitive surface, a light guide interposed between and optically coupling said scintillator and said photosensitive surface, and an electrical signal control element; a pulse processing and display unit located remotely from said probe and including a differential discriminator for receiving electrical pulses from said photodetector; and a pulse recorder means connected to the output of said differential discriminator and connected to said electrical signal control element, whereby operation of said pulse recorder means is controlled by said signal control element; wherein said pulse recorder means is equipped with a timer means, a mode selection switch alternatively movable between a count rate mode position and a percentage mode position, a digital register operable connected to said differential discriminator, to said electrical signal control element, and to said timer means and which accumulates pulses from said differential discriminator for an interval of time determined under the control of said timer means and said mode selection switch as initiated by said electrical signal control element, and further including a reference count digital storage circuit operably connected to said differential discriminator by means of said mode selection switch, a frequency burst generator circuit connected to said differential discriminator and connected to said time control circuit and connected to programmable digital frequency divider circuit means connected to said digital storage circuit and to said frequency burst generator circuit, and a counter means operated under the control of said mode selection switch for receiving an input from said programmable digital frequency divider circuit to accumulate a ratio of the pulses from said discriminator to the pulses previously counted and stored in said digital storage circuit and increased by the factor of said frequency burst generator circuit so that the final accumulated count represents a percentage.

4. The instrument of claim 2 further comprising a printer actuable by said electrical signal control element for printing the contents of said counter means.

5. The fibrinogen monitor of claim 4 wherein said pulse processing and display unit includes a battery voltage monitoring circuit connected to provide an inhibit signal whenever the battery voltage is below the predetermined level required to assure accurate signal processing and a display control circuit connected to said battery voltage monitoring circuit so as to inhibit the display of data whenever said inhibit signal is received from said battery voltage monitoring circuit.

6. The instrument of claim 2 wherein a sequence error signaling circuit is provided and is actuable by said mode selection switch to inhibit said pulse recorder means and provide an error indication whenever said mode selection switch is in the percentage mode position without first having been in the count rate mode position and storing a statistical count of pulses in said reference count digital storage register.

7. A fibrinogen monitor for detecting and determining the extent of quantities of fibrinogen tracer-labeled with the radioisotope Iodine-125 comprising a scintillation probe including a photodetector having a photosensitive face, a crystalline disc of thallium activated sodium iodide in optical communication with said photodetector and positioned at an angle with respect to the photosensitive face of said photodetector, a light conductor positioned between said disc and said photosensitive face, and an electrical signal control element all connected to a separate pulse processing and display unit that includes a discriminator circuit responsive to pulses produced by said photodetector due to the light pulses resulting from the radioactive emissions from Iodine-125, and a pulse recorder means activated by said electrical signal control element for receiving outputs from said discriminator circuit.

8. The fibrinogen monitor of claim 7 wherein said pulse processing and display unit includes a ratemeter circuit which displays a rate of pulses from said discriminator circuit.

9. The fibrinogen monitor of claim 8 further including an interval control circuit and wherein said ratemeter circuit also connects to said interval control circuit whereby the sensitivity of said ratemeter circuit is proportional to the time interval setting of said interval control circuit so that the output of said ratemeter circuit will be directly indicative of the expected total pulses accumulated from said discriminator during said time interval for any time interval set into said time interval circuit.

10. The fibrinogen monitor of claim 9 wherein the output of said ratemeter circuit is displayed on a panel meter in terms of the standard deviation expected for the next count to be taken by said pulse processing and display unit and further that the scale of said panel meter is calibrated in terms of expected standard deviation for any time interval setting of said time interval control circuit.

11. The fibrinogen monitor of claim 9 wherein said pulse processing and display unit further includes a monitor circuit connected to said ratemeter circuit to produce a rejection signal output whenever the subsequent rate of pulses times the interval time setting is less than a predetermined level and a rejection circuit connected to disable said pulse recorder means and to illuminate a rejection indicator thus preventing data collection using time intervals which are too short and activity levels which are too low to yield data with a standard deviation which is less than a predetermined level.

12. The fibrinogen monitor of claim 11 wherein said pulse processing and display unit includes an audible alarm connected to said monitor circuit so as to provide an audible alarm whenever the expected standard deviation is above said predetermined level at any time during said time interval.

13. The fibrinogen monitor of claim 12 wherein said pulse processing and display unit includes a switch connected to said audible alarm such that the operator may inhibit said audible alarm whenever it might create excessive disturbance.

14. The fibrinogen monitor of claim 11 wherein said batteries may be recharged while installed in said pulse processing and display unit by an external charger connected to said pulse processing and display unit by connector means which is interlocked such that said pulse processing and display unit is totally inhibited from operation while said external charger is connected to said pulse processing and display unit thus precluding the possibility of electrical shock to the patient and/or the operator due to a shorted circuit which might create a direct or indirect connection to line power if said interlock were not provided.

15. The fibrinogen monitor of claim 7 further characterized in that a photodetector gain adjustment circuit is provided.

16. The fibrinogen monitor of claim 7 wherein said scintillation probe is connected by cord to said pulse processing and display unit, and a recess is defined in the carrying handle of said pulse processing and display unit whereby said scintillation probe is snugly and removably seated therein in a reproducible position.

17. The fibrinogen monitor of claim 7 wherein said pulse processing and display unit is provided with a stable low level radiation source at said reproducible position for use in pulse amplitude calibration using said gain adjustment circuit.

18. The fibrinogen monitor of claim 7 wherein said pulse processing and display unit includes an audible indicator for signaling the end of each pulse counting and processing interval so as to allow an operator to direct full attention to maintaining the probe position without the need to visually check said pulse processing and display unit in order to determine when pulse counting and processing has been completed.

19. The fibrinogen monitor of claim 18 wherein the pulse processing and display unit includes a switch connected to said audible indicator such as the operator may inhibit said audible indicator whenever it might create excessive disturbance.

20. The fibrinogen monitor of claim 7 wherein the mounting of said stable low level radiation source incorporates a collimator such that the radiation from said stable low level radiation source is collimated into a beam which is small relative to the diameter of said scintillation crystal so that small changes in the position of said scintillation crystal relative to said stable low level radiation source either in terms of distance or in terms of lateral position will have no significant affect on the pulse rate from said photodetectors.

21. The fibrinogen monitor of claim 7 wherein said pulse processing and display unit includes a frequency-phase amplitude demultiplexing circuit such that said probe is connected to said pulse processing and display unit via a single coaxial cable comprised of a single conductor in a shield such that pulses from said photodetector and said electrical signal control element to said pulse processing and display unit and power from said pulse processing and display to said probe are concurrently transmitted over said single cable.

22. The fibrinogen monitor of claim 7 wherein the pulse processing and display unit includes an audible alarm connected to said sequence error signalling circuit so as to provide an audible indication when said sequence error signalling circuit has detected an error condition.

23. The fibrinogen monitor of claim 22 wherein said pulse processing and display unit includes a switch connected to said audible alarm such that the operator may inhibit said audible alarm whenever it might create excessive disturbance.

24. A fibrinogen monitor for detecting and determining the extent of quantities of fibrinogen tracer-labeled with the radioisotope Iodine-125 comprising a scintillation probe including a photodetector, a crystal of thallium activated sodium iodide in optical communication with said photodetector, and an electrical signal control element all connected to a separate pulse processing and display unit that includes a discriminator circuit responsive to radioactive emissions from Iodine-125, and a pulse recorder means activated by said electrical signal control element for receiving outputs from said discriminator circuit.

25. The fibrinogen monitor of claim 24 further including a power source in the form of removable, rechargeable batteries.

26. The fibrinogen monitor of claim 24 further including timing means actuable by said electrical signal control element to control said pulse recorder means to count signals from said photodetector for a predetermined interval of time.

27. The fibrinogen monitor of claim 24 wherein said timing means includes an adjustment to select one of several predetermined time intervals.

* * * * *